(12) United States Patent  
Leyva

(10) Patent No.: US 9,089,621 B1  
(45) Date of Patent: Jul. 28, 2015

(54) ORGANIC FLOWER SCENT DISPENSER

(71) Applicant: Cesar Leyva, Sylmar, CA (US)

(72) Inventor: Cesar Leyva, Sylmar, CA (US)

( * ) Notice: Subject to any disclaimer, the term of this patent is extended or adjusted under 35 U.S.C. 154(b) by 162 days.

(21) Appl. No.: 14/033,330

(22) Filed: Sep. 20, 2013

Related U.S. Application Data

(60) Provisional application No. 61/704,160, filed on Sep. 21, 2012.

(51) Int. Cl.
*B01F 3/04* (2006.01)
*A01G 5/00* (2006.01)
*A61L 9/12* (2006.01)

(52) U.S. Cl.
CPC . *A61L 9/122* (2013.01); *A01G 5/00* (2013.01); *B01F 3/04* (2013.01)

(58) Field of Classification Search
CPC ..................................... A01G 5/00; B01F 3/04

USPC ............. 261/119.1, DIG. 88; 47/41.01, 41.13
See application file for complete search history.

(56) References Cited

U.S. PATENT DOCUMENTS 1,694,214 A * 12/1928 Ginder .............................. 415/8

\* cited by examiner

*Primary Examiner* — Robert A Hopkins
(74) *Attorney, Agent, or Firm* — Brooks Acordia IP Law, PC; Pejman Yedidsion; Christopher Weiss

(57) ABSTRACT

A device for dispensing organic scents comprising a base assembly; a controller; a bowl assembly; at least one screen disposed within the bowl assembly having a plurality of apertures configured to hold one or more flowers; at least one row of air inlets proximate to one or more flowers; a top assembly having an angled top surface and at least one vent; and a fan electrically connected to the controller, where the controller may be configured to turn the fan on continuously, cycle the fan between on and off modes, or turn the fan off responsive to a user input.

20 Claims, 12 Drawing Sheets

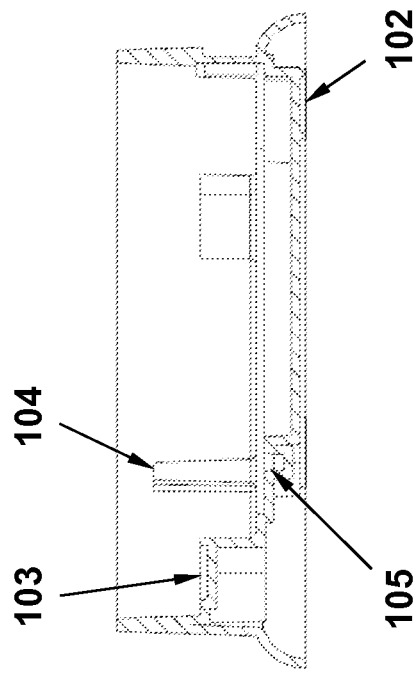
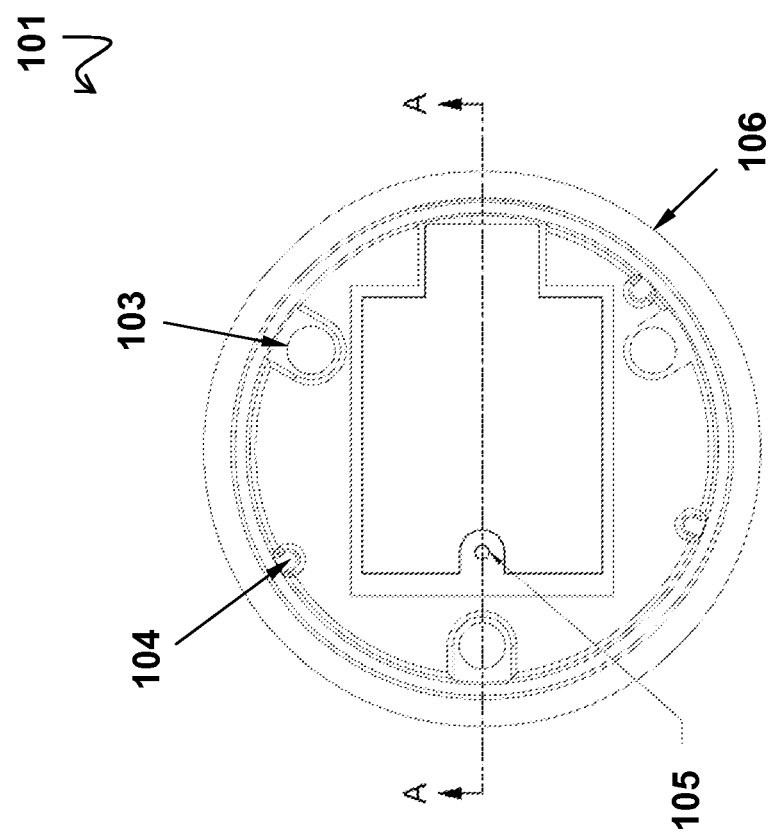
FIG. 2B
FIG. 2A

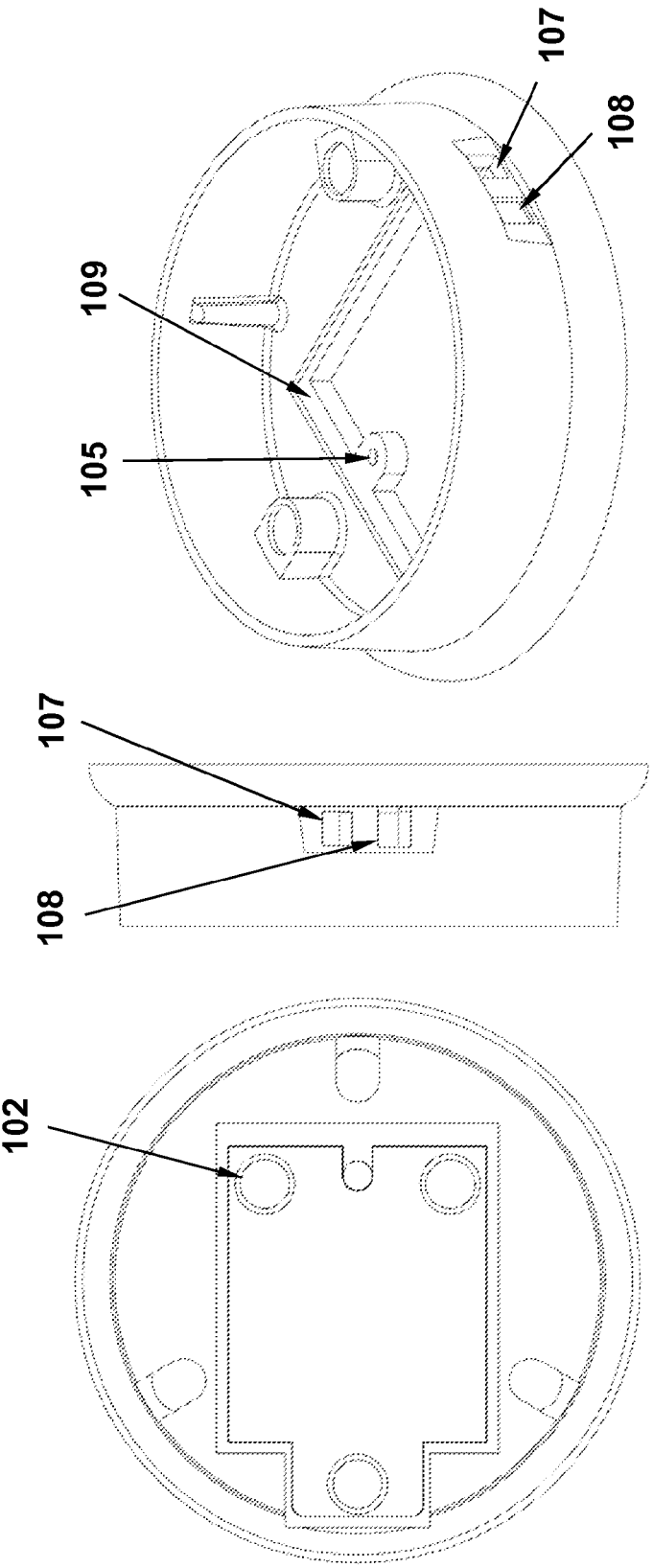

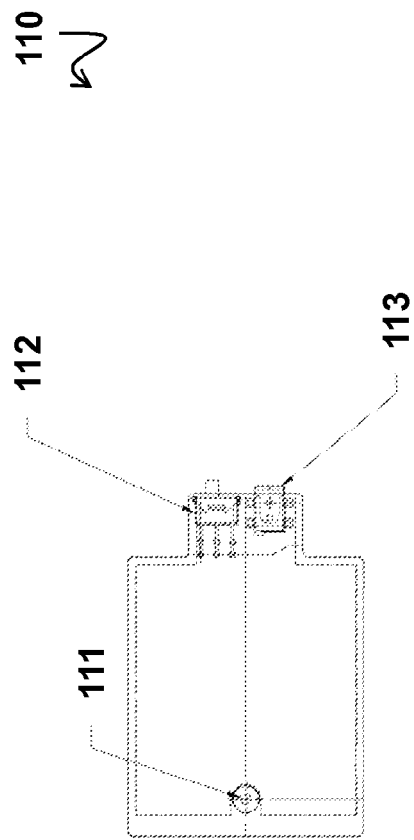
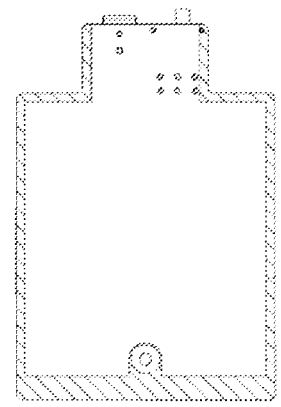
FIG. 3A
FIG. 3B
FIG. 3C

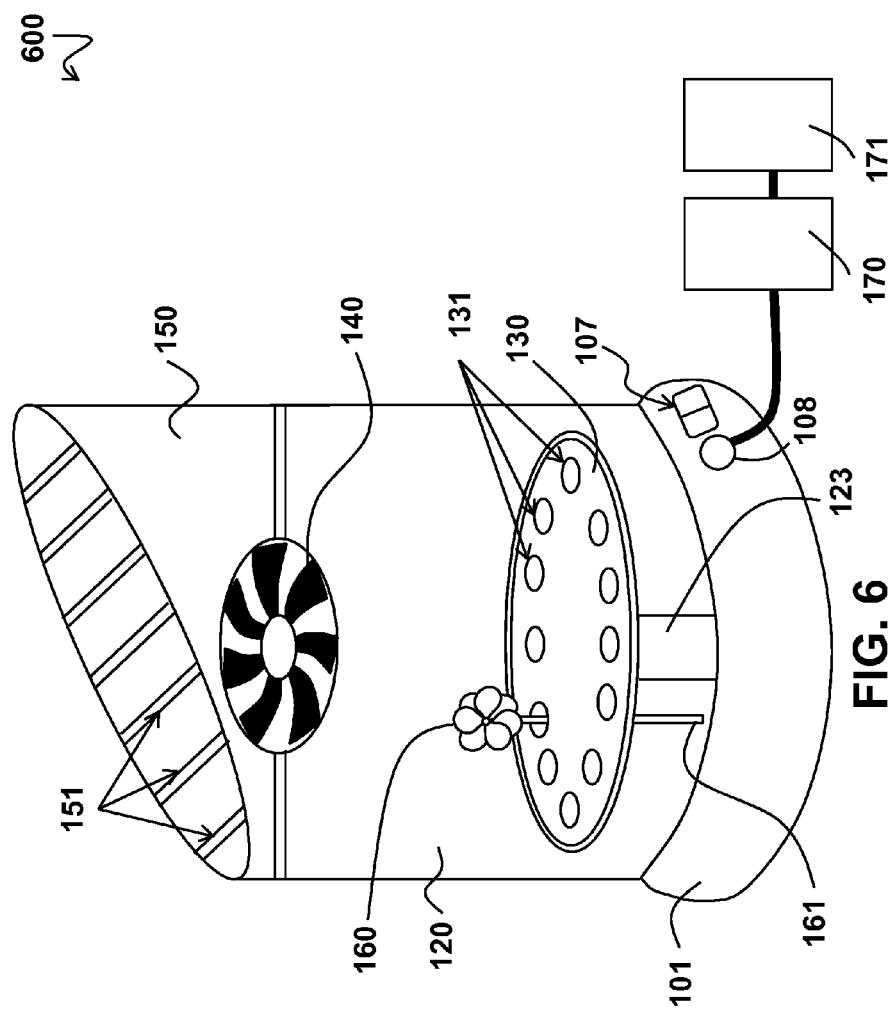

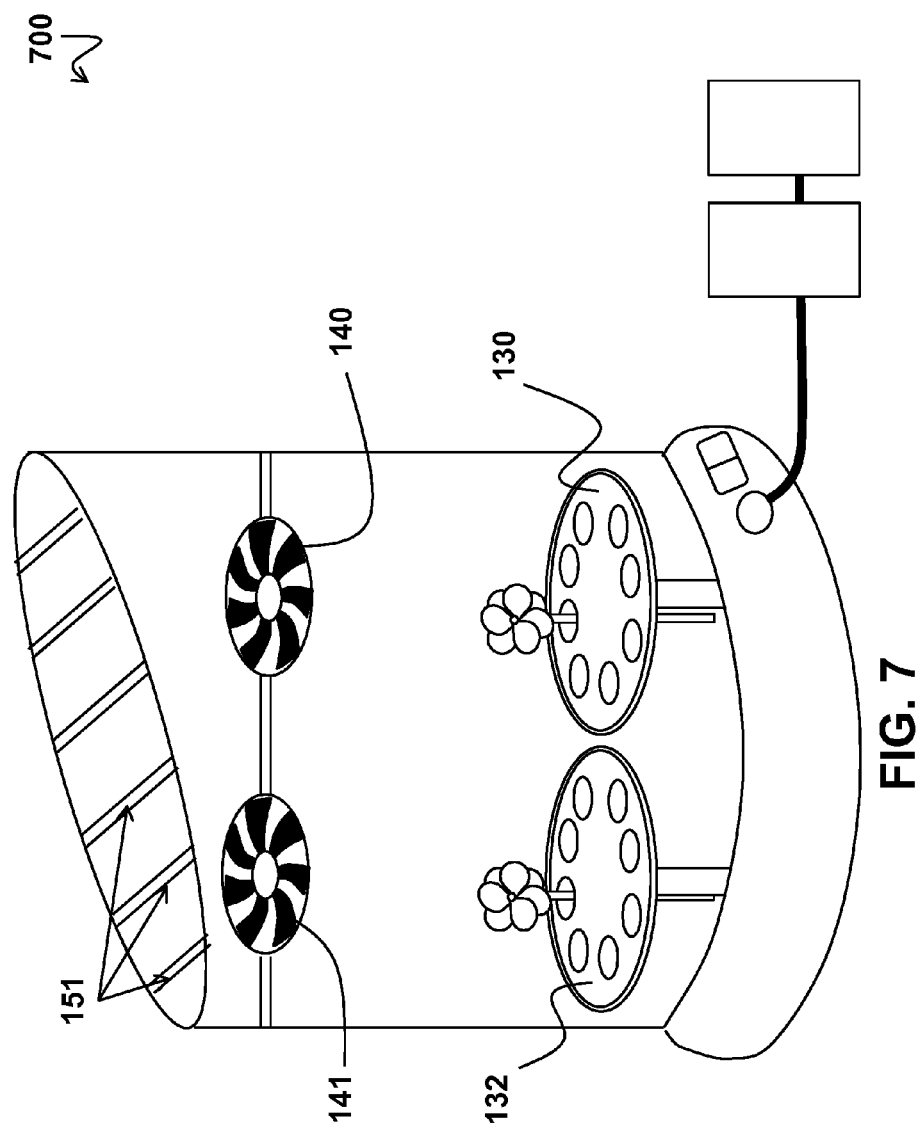

ORGANIC FLOWER SCENT DISPENSER

CROSS-REFERENCE TO RELATED APPLICATION

This application claims the benefit of U.S. Provisional Patent Application Ser. No. 61/704,160 filed Sep. 21, 2012, which is hereby incorporated by reference herein for all purposes.

FIELD OF ENDEAVOR

Embodiments of the present invention pertain to scent dispensers and particularly to scent dispensers utilizing natural scents.

SUMMARY

Exemplary embodiments may comprise a device that may comprise: a base assembly comprising one or more alignment grooves; a controller disposed within the base assembly; a bowl assembly comprising one or more alignment grooves, where the bowl assembly is configured to detachably attach to the base assembly, and where the one or more alignment grooves of the base assembly are configured to align with the one or more alignment grooves of the bowl assembly; at least one screen disposed within the bowl assembly in a position parallel to a bottom surface of the bowl assembly, where the at least one screen comprises a plurality of apertures configured to hold one or more flowers; at least one row of air inlets on the surface of the bowl assembly at a vertical position above the at least one screen and proximate to a position of the space configured to hold one or more flower; a top assembly configured to detachably attach from the bowl assembly, wherein the top element comprises an angled top surface and at least one vent; and a fan disposed within the top assembly, where the fan is electrically connected to the controller within the base assembly by a detachably attached electrical conduit in the bowl assembly; where the controller is configured to execute at least one of: turn the fan on continuously responsive to a user input, cycle the fan between on and off modes at a regular set interval of time responsive to a user input, and turn the fan off responsive to a user input. In additional exemplary embodiments, the device may further comprise one or more lights.

In additional exemplary embodiments, the one or more lights may be configured, by the controller, to turn on during at least one of: when the fan is on, and when the fan is cycling between on and off modes. In additional exemplary embodiments, the device may further comprise one or more speakers. In additional exemplary embodiments, the one or more speakers may be configured, by the controller, to turn on during at least one of: when the fan is on, and when the fan is cycling between on and off modes. In additional exemplary embodiments, the user input may be at least one of: a two-way switch, a three-way switch, and a prompt from a remote device. In additional exemplary embodiments, the remote device may be at least one of: a web application and a smartphone application. In additional exemplary embodiments, the bowl assembly may further comprise a screen support, where the screen support may be configured to detachably attach to the screen. In additional exemplary embodiments, the screen support may be configured to detachably attach to the screen by at least one of: a screw, a press fit, and one or more magnets. In additional exemplary embodiments, the device may further comprise a second screen comprising a plurality of apertures, and the second screen may detachably attach to the screen support. In additional exemplary embodiments, the second screen may be vertically separated from the first screen by a distance, and the plurality of apertures of the second screen may vertically align with the plurality of apertures of the screen.

In additional exemplary embodiments, the fan may further comprise a fan mounting ring, and the fan mounting ring may be detachably attached to the top assembly. In additional exemplary embodiments, there may be a second fan and a second screen and/or a third fan and a third screen. In additional exemplary embodiments, there may be a suction cup mount. In additional exemplary embodiments, at least one vent may be movable to direct air from the fan in a first direction and/or a second direction. In additional exemplary embodiments, a bottom portion of the bowl assembly vertically below the at least one screen may be configured to hold a liquid. In additional exemplary embodiments, the bowl assembly may further comprise an indent configured to guide any liquid being emptied from the bowl assembly. In additional exemplary embodiments, the indent may further comprise the electrical conduit. In additional exemplary embodiments, the base may further comprise a rim. In additional exemplary embodiments, the device may further comprise a flower stem cutter.

BRIEF DESCRIPTION OF THE DRAWINGS

Embodiments are illustrated by way of example and not limitation in the figures of the accompanying drawings, and in which:

FIG. 2A depicts a top view of a base assembly of an exemplary scent dispenser system;

FIG. 2B depicts a cross-sectional view of the base assembly in FIG. 2A;

FIG. 2C depicts a bottom view of a base assembly of an exemplary scent dispenser system;

FIG. 2D depicts a side view of a base assembly of an exemplary scent dispenser system;

FIG. 2E depicts a perspective view of a base assembly of an exemplary scent dispenser system;

FIG. 3A depicts a top view of a printed circuit board assembly ("PCBA") of an exemplary scent dispenser system;

FIG. 3B depicts a side view of a PCBA of an exemplary scent dispenser system;

FIG. 3C depicts a bottom view of a PCBA of an exemplary scent dispenser system;

FIG. 6 depicts an exemplary scent dispenser system with one tray and one fan;

FIG. 7 depicts an exemplary scent dispenser system with two trays and two fans;

DETAILED DESCRIPTION

Figure 1:
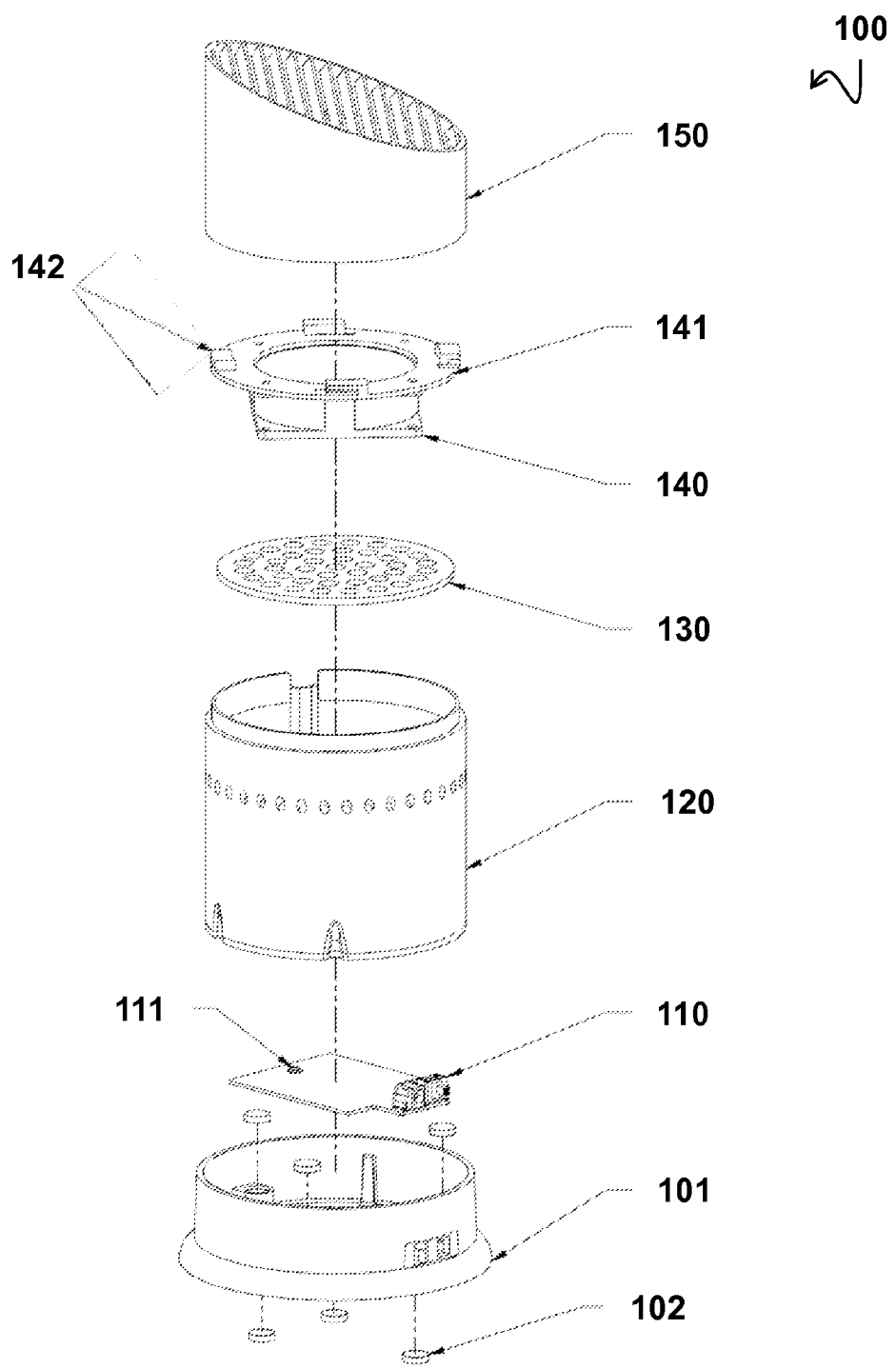
FIG. 1 depicts a partial exploded view of an exemplary scent dispenser system.

FIG. 1 depicts a partial exploded view of an exemplary scent dispenser system 100. The scent dispenser system may comprise a base assembly 101. The base assembly 101 may have one or more points of contact, e.g., rubber feet 102, with a surface to improve stability of the system. The system may also include a printed circuit board assembly ("PCBA") 110. The PCBA 110 may be attached to the base assembly 101 by a connector, e.g., a pan head screw 111. The system may also comprise a bowl assembly 120. The bowl assembly 120 may be sealed at the bottom so that it may be partially filled with water, liquids, and/or other nutrients. The system may also include a screen 130. The screen 130 may be disposed inside of the bowl assembly 120 and parallel to the base 101. In some embodiments, the system may comprise two or more screens of varying size and/or having varying apertures (not shown). These screens may then be switched out depending on the thickness of the stems, the flowers being utilized, or user preference. A larger screen aperture may allow for more than one stem per aperture and may result in a more clustered appearance. The system may also comprise a fan 140, e.g., an 80 mm fan used for central processing unit ("CPU") cooling. The fan 140 may be attached to a fan mounting ring 141. The fan mounting ring 141 may comprise one or more mounting devices 142. These mounting devices 142 may be used to secure the fan mounting ring 141 and attached fan 140 to a system top assembly 150. The top assembly 150 may be placed over a flange of the bowl assembly 120 so as to create a seamless appearance. In some embodiments, the system may also include a built-in plant stem cutter and/or trimmer for ease of use. This cutter may be revealed upon disassembly, e.g., hidden in the top assembly 150 or the base assembly 101, so as to improve safety. The cutter may also include one or more guards so as to protect a user.

FIG. 2A depicts a top view of a base assembly of an exemplary scent dispenser system 101. The base assembly 101 may comprise one or more spacers 103. The spacers may be used to provide durability, shock-support, and/or reduce scratching of the bottom surface of a bowl assembly (see FIGS. 4A-4C), which may be placed on top of the base assembly 101. The base assembly may also comprise one or more grooves 104 for ensuring alignment with the bowl. In some embodiments, the grooves 104 may not be equidistant so that the bowl may only be positioned in one direction. This may ensure the alignment of any electrical contacts going to the fan or other electronics. The base assembly may also comprise a point of attachment for a PCBA (see FIGS. 3A-3C) to the base, e.g., a threaded hole 105 for receiving a screw. The base assembly 101 may also comprise a rim 106 extending around the base assembly 101 so as to provide increased stability.

FIG. 2B depicts a cross-sectional view of the base assembly in FIG. 2A across the line A-A. The base may comprise one or more rubber feet 102 so as to provide increased friction, protect a surface from scratches when the base may be placed on the surface, and/or for noise dampening. The one or more spacers 103 may provide a gap between the PCBA (not shown) and the bowl assembly (not shown) when inserted into the base assembly. The one or more grooves 104 may provide alignment for the bowl assembly. The walls of the base assembly may be tall enough to conceal the one or more spacers 103 and one or more grooves 104. The threaded hole 105 may extend into a bottom portion of the base assembly to secure a PCBA to the base assembly.

FIG. 2C depicts a bottom view of a base assembly of an exemplary scent dispenser system. The one or more rubber feet 102 may be attached to the bottom of the base assembly or to the bottom of a PCBA.

FIG. 2D depicts a side view of a base assembly of an exemplary scent dispenser system. The base assembly may comprise one or more cut-outs. One of these cut-outs may be for a switch 107. This switch cut-out 107 may be for an on-off switch or a three-way switch. In some embodiments, the switch may be replaced with, or in addition to, an infrared ("IR") receiver, a Bluetooth® antenna, and/or a Wi-Fi antenna. Another of these cut-outs may be for a power cable input 108. This power cable input 108 may be from a standard 12V adapter to provide power to the PCBA and/or the fan.

FIG. 2E depicts a perspective view of a base assembly of an exemplary scent dispenser system. The base assembly may comprise a PCBA cut-out 109 to ensure proper fit and alignment of the PCBA in the base assembly. The PCBA may then be secured to the base assembly once in place by fastening a screw through the threaded hole 105.

FIG. 3A depicts a top view of a printed circuit board assembly ("PCBA") of an exemplary scent dispenser system. The PCBA may comprise a screw 111 for securing the PCBA to the base assembly. The PCBA may also comprise a switch 112, e.g., a two-way switch or a three-way switch. The PCBA may also comprise a power connector 113, e.g., a direct current (DC) power jack connector. The switch 112 and power connector 113 may fit through the cut-outs in the base assembly (107 and 108, respectively, see FIG. 2D). In some embodiments, the PCBA may further comprise a wireless receiver (not shown), e.g., a Bluetooth® antenna and/or a WiFi antenna. In other embodiments, the PCBA may further comprise a processor having addressable memory and configured to send and receive signals to turn the fan on or off based on an input from a remote device (not shown), e.g., an application on a web browser, iPhone®, and/or Android device. In some embodiments, the system may further comprise one or more lights and/or speakers (not shown), which may also be controlled remotely. FIG. 3B depicts a side view of a PCBA of an exemplary scent dispenser system. FIG. 3C depicts a bottom view of a PCBA of an exemplary scent dispenser system.

Figure 4A:
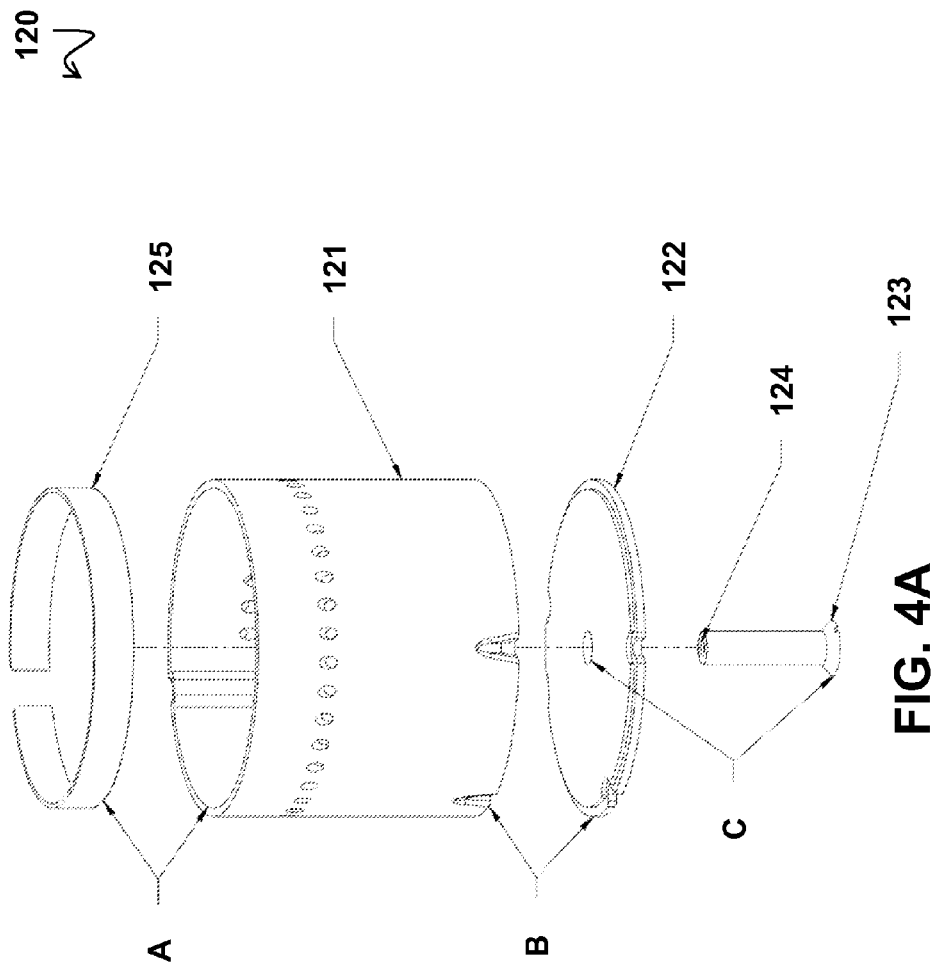
FIG. 4A depicts an exploded view of a bowl assembly of an exemplary scent dispenser system.

FIG. 4A depicts an exploded view of a bowl assembly 120 of an exemplary scent dispenser system. The bowl assembly 120 may comprise a bowl 121. This bowl 121 may comprise a substantially circular cross-section with an indent for an electrical connection/power cables. In other embodiments, the bowl 121 may have a substantially polygonal cross-section. The bowl assembly may also comprise a bowl base 122. The bowl base 122 may comprise a cut-out for a screen support 123 to be inserted. The screen support 123 and accompanying cut-out may have a circular cross-section. In other embodiments, the screen support 123 and accompanying cut-out may have a polygonal cross-section. The base of the screen support 123 may have a flared end to match a corresponding feature on the underside of the bowl base, so as to create a smooth surface on the underside of the bowl base 122 and/or ensure a proper water-tight fit. The top of the screen support may comprise a screen attachment point 124. This screen attachment point may be a threaded hole for a screw, an indentation for a corresponding feature on the underside of the screen, and/or a magnet to detachably attach the screen to the screen support 123. The bowl assembly 120 may also comprise a flange 125. The flange 125 may be used to align the bowl 121 with the top assembly. In one embodiment the bowl 121 and flange 125 may be made of a clear material, e.g., acrylic. The bowl base 122 may be made of an opaque material, e.g., black acrylic, so as to conceal any electronics in the base assembly. The screen support 123 may also be made of an opaque material, e.g., black acrylic. The components of the bowl assembly 120 may be joined at points A, B, and C by an adhesive, e.g., a permanent clear adhesive. The adhesive used at points B and C may be water-tight. In some embodiments, the components of the bowl assembly 120 may be further divided and/or combined.

Figure 4C:
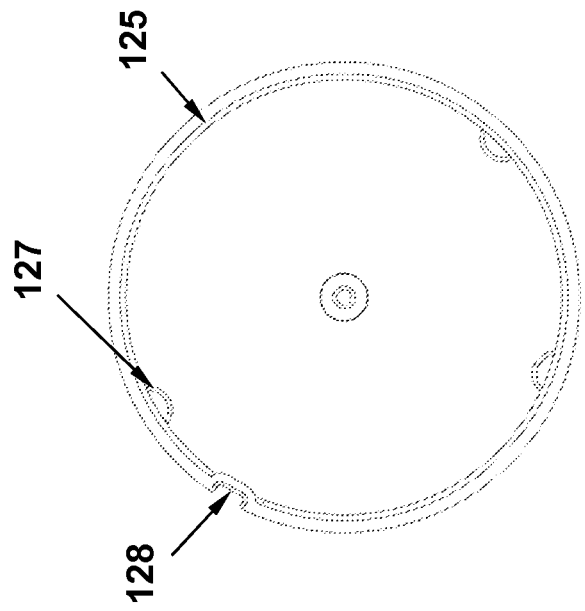
FIG. 4C depicts a top view of a bowl assembly of an exemplary scent dispenser system.
Figure 4B:
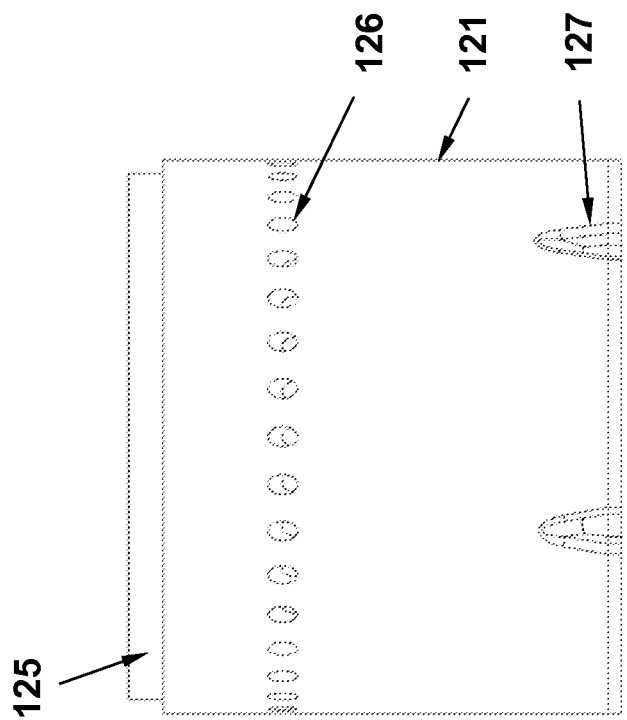
FIG. 4B depicts a side view of a bowl assembly of an exemplary scent dispenser system.

FIG. 4B depicts a side view of a bowl assembly of an exemplary scent dispenser system. The bowl 121 of the bowl assembly may comprise one or more concentric rows of air inlets 126 disposed in an upper portion of the bowl 121. When the screen (130, see FIG. 1) is placed in the bowl assembly, flowers placed in the screen will be disposed inside the bowl assembly proximate to the one or more concentric rows of air inlets 126. Air may flow in through the air inlets 126, past the proximate flowers, and up through the fan into the top assembly. Accordingly, the system is more efficient in dispersing the scent of the flowers due to the placement of the air inlets 126. The bowl 121 may also be attached to the flange 125, which provides a space for the top assembly to attach to the bowl assembly. The grooves 127 in the bowl 121 allow for alignment with the base assembly.

FIG. 4C depicts a top view of a bowl assembly of an exemplary scent dispenser system. The screen support 123 may be disposed in the center of the bowl assembly. The flange 125 may be disposed concentric with the bowl assembly so that the top assembly is aligned to rest on the top of the bowl when attached. In some embodiments, the flange 125 may further comprise threads and/or magnets to ensure a secure fit of the top assembly with the bowl assembly. The bowl assembly may also comprise an indent 128 for running power cables from the base assembly to the fan in the top assembly. This indent may be properly aligned with the base via the grooves 127 in the bowl (see FIG. 4B). In some embodiments, this indent may be used to channel water cleanly out of the bowl 121 for cleaning and/or refilling the bowl.

Figure 5A:
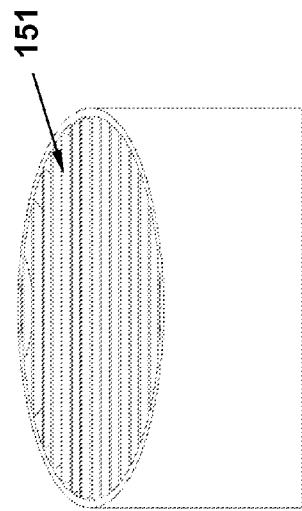
FIG. 5A depicts a side view of a top assembly of an exemplary scent dispenser system.

FIG. 5A depicts a side view of a top assembly 150 of an exemplary scent dispenser system. The top assembly 150 may have an angled top. This angled top may prevent the inadvertent placement of objects on top of the system, which may block airflow. The angled top may also prevent the accumulation of dust and/or other debris on or in the system.

Figure 5B:
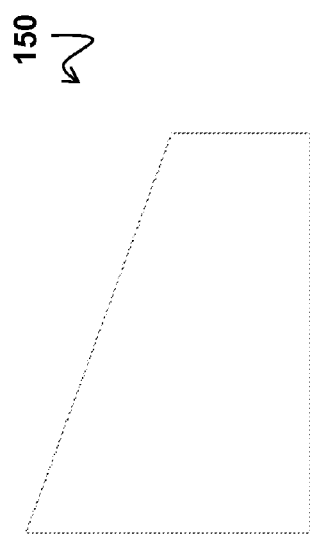
FIG. 5B depicts a front view of a top assembly of an exemplary scent dispenser system.

FIG. 5B depicts a front view of a top assembly of an exemplary scent dispenser system. The top assembly may comprise one or more vents 151. The one or more vents 151 may be fixed or adjustable. In some embodiments, the vents 151 may be adjusted to direct air flow in two or more directions.

Figure 5C:
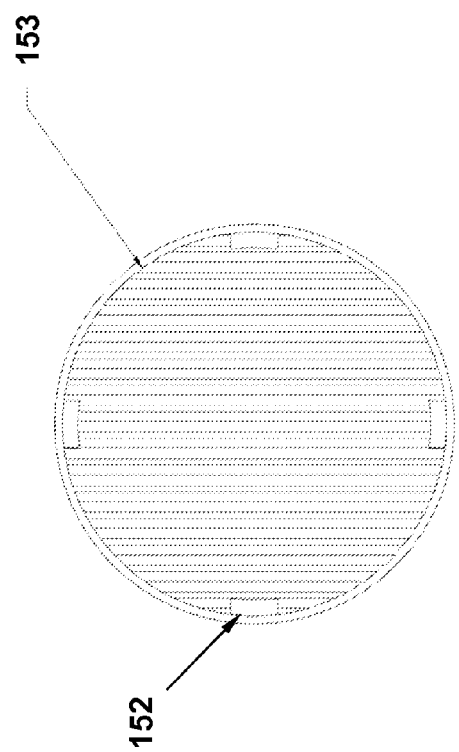
FIG. 5C depicts a bottom view of a top assembly of an exemplary scent dispenser system.

FIG. 5C depicts a bottom view of a top assembly of an exemplary scent dispenser system. The inner wall 153 of the top assembly may be in contact with an outer wall of the flange (125, see FIG. 4B) when the top assembly is attached to the bowl assembly. In some embodiments, the inner wall 153 of the top assembly may comprise threads and/or magnets to ensure a secure fit. The top assembly may also comprise one or more mounting points 152. These mounting points 152 may be used to connect the top assembly to the one or more mounting devices (142, see FIG. 1) of the fan mounting ring (141, see FIG. 1) by, e.g., a twisting motion. This top assembly may be composed of an opaque material, e.g., black acrylonitrile butadiene styrene ("ABS"), so as to conceal the fan and/or wires inside the top assembly.

FIG. 6 depicts an exemplary scent dispenser system 600 with one tray 130 and one fan 140. The scent dispenser system may comprise a base assembly 101 made from an opaque material. In some embodiments, the base assembly 101 may be made from a transparent material. The base assembly 101 may contain a power connection 108, e.g., a 12 VDC input, from a DC transformer 170 connected to a power source 171, e.g., a 115 V power outlet. In some embodiments, the power source 171 may be a battery, which may be concealed in the base assembly. The base assembly 101 may also comprise a switch 107 that may allow a user to turn the system to an ON position, i.e., deliver power to the fan 140, or an off position, i.e., cut-off power to the fan 140. In some exemplary embodiments, the base assembly 101 may comprise a controller (see FIGS. 3A-3C) which may give the user the option to leave the system 600 constantly on or to put the system 600 into an "Auto" position, which cycles the fan 140 to run at regular intervals, e.g., seven minutes on and seven minutes off.

The exemplary scent dispenser system 600 may also comprise a bowl assembly 120 on top of the base assembly 101. This bowl assembly 120 may be made of a transparent material so as to allow a user to view the contents inside the bowl assembly 120. There may be a detachably attached screen 130 and corresponding screen support 123 inside the bowl assembly 120. In some embodiments, each screen 130 may comprise two or more screen portions with a vertical gap between each portion. A plant with a stem, e.g., a flower, may be inserted into the screen 130 and the gap between each portion may assist in keeping the stem of the plant in an upright position (not shown). The screen 130 may comprise one or more apertures 131 to allow for the upright placement of one or more floral arrangements, e.g., flowers, in the system 600. The apertures 131 may be the same size or may be various sizes to accommodate two or more plant stem diameters. In some embodiments, the bowl assembly 120 may be partially filled with water and/or other nutrients, to give nutrients to the one or more flowers 160 via the flower stems 161. This may elongate the duration of use of the one or more flowers 160 before requiring replacement. In some embodiments, there may be a drainage hole in the bowl assembly 120 to allow for the draining of water contained in the bowl assembly 120 without requiring the system 600 be disassembled (not shown). In other embodiments, there may be a drainage hole in the bowl assembly 120 that aligns with a drainage hole in the base assembly 101 to allow for the discreet removal of water from the bottom of the base assembly 101 without interrupting the visual appearance of the transparent sides of the bowl assembly 120. The bowl assembly 120 may be detachably attached so as to be removable from the base assembly 101 and top assembly 150 for cleaning and/or to add water to the system 600.

The exemplary scent dispenser system 600 may also comprise a top assembly 150 disposed above the bowl assembly 120. This top assembly 150 may be made of an opaque material. A fan 140 may be disposed inside the top assembly 150. The fan 140 may receive power from electrical cables (128, see FIG. 4C) that may run up the side of the bowl assembly 120 from the base assembly 101. In some embodiments, the power to the fan 140 may be run through a center column (not shown) than extends from the base assembly 101 to the top assembly 150. This center column may be transparent or opaque, so as to hide the electrical and/or control cables inside. In some embodiments, the bowl assembly 120 may be a tubular shape to fit over the center column, so as to provide guidance in reassembly and ensure a watertight fit. In some embodiments, the power cables may be detachable so that the bowl assembly 120 may be removed and cleaned. The fan 140 may be designed so as to limit noise while still providing adequate air flow to allow for dispersion of the enclosed scents. For example, the fan specifications may be 12 V, sixteen cubic feet per minute ("CFM"). The top of the system 600 may be at a slanted angle in relation to the horizontal surface below and covered in one or more vents 151. In an exemplary embodiment, these vents 151 may be angled to direct airflow, and accompanying scents, in one or more user desired directions.

FIG. 7 depicts an exemplary scent dispenser system 700 with two screens 130,132 and two fans 140,141. In an exemplary embodiment, the system 700 may have an elongated oval cross-section to allow for the placement of an additional screen 132 and a corresponding additional fan 141. In this exemplary embodiment, the fans 140,141 may be positioned directly above their respective screens 130,132. In some embodiments, the fans 140,141 may be positioned directly above the corresponding screens 130,132 so as to provide optimal scent dispersion. In an exemplary embodiment, the vents 151 may be positioned to direct airflow, and accompanying scents, in two or more user defined directions. For example, the vents above each fan 140,141 may be directed in two different directions.

Figure 8:
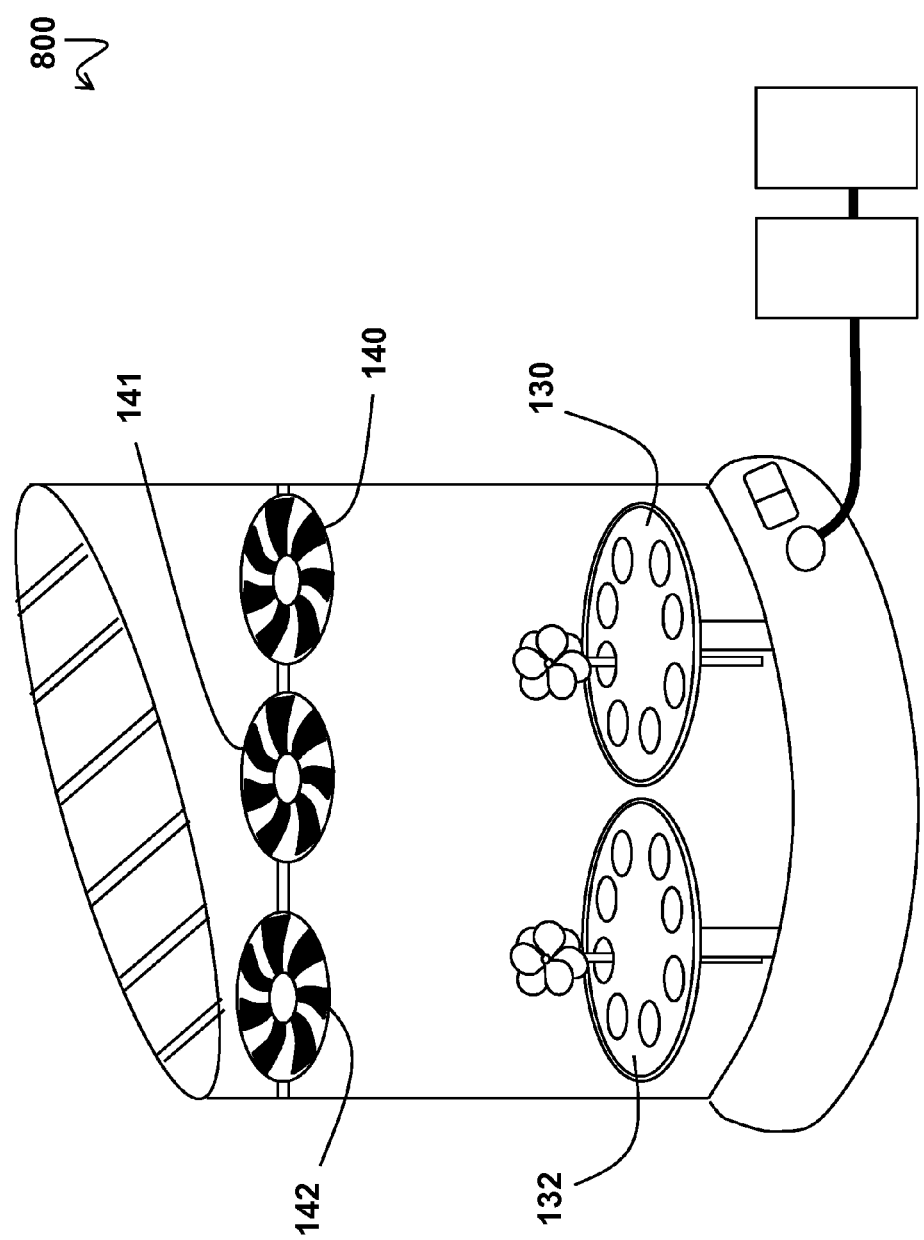
FIG. 8 depicts an exemplary scent dispenser system with two trays and three fans.

FIG. 8 depicts an exemplary scent dispenser system 800 with two screens 130,132 and three fans 140,141,142. In this exemplary embodiment, the screens 130,132 may be sized to accept a greater number of cut flowers. In some embodiments, the system 800 may comprise one or more lights, e.g., Light-Emitting Diodes (LED), to illuminate the system 800 and any cut flowers placed inside the system 800. In other embodiments, the system 800 may comprise one or more speakers to play a pre-recorded noise or live broadcast, e.g., music, ambient sounds, or white noise.

Figure 9:
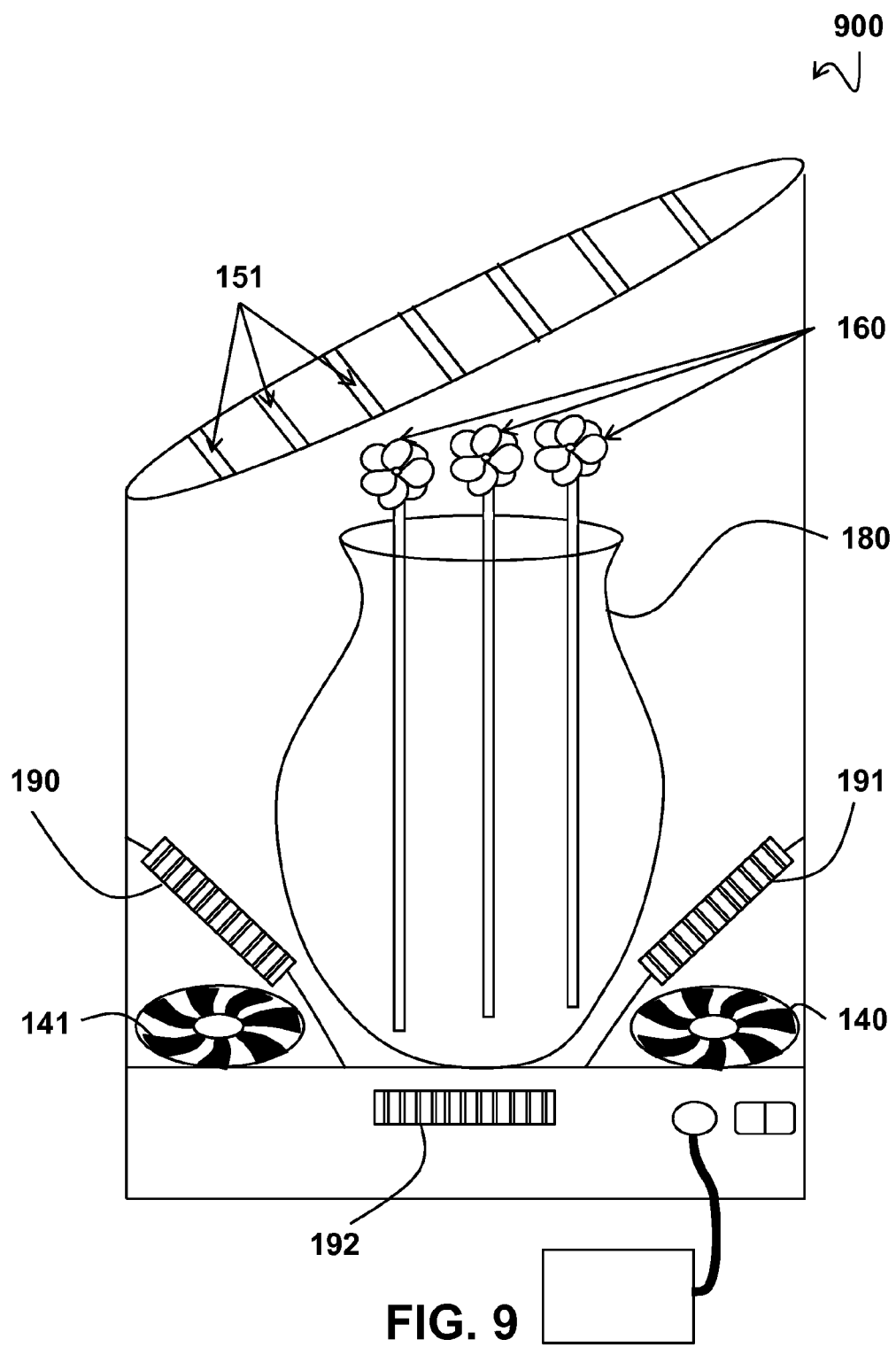
FIG. 9 depicts an exemplary scent dispenser system for holding a vase.

FIG. 9 depicts an exemplary scent dispenser system 900 for holding a vase 180. In an exemplary embodiment, the system 900 may comprise one or more vents 190,191,192 to draw in air which is then pushed past the one or more flowers 160 in the vase 180 and out of the system 900 via the vents 151. In some embodiments, the vase 180 may be fixed to the system 900. In other embodiments, the vase 190 may be removable for cleaning. The vase 190 may be included as part of the system 900 and/or supplied by the user to accommodate individual preferences.

Figure 10:
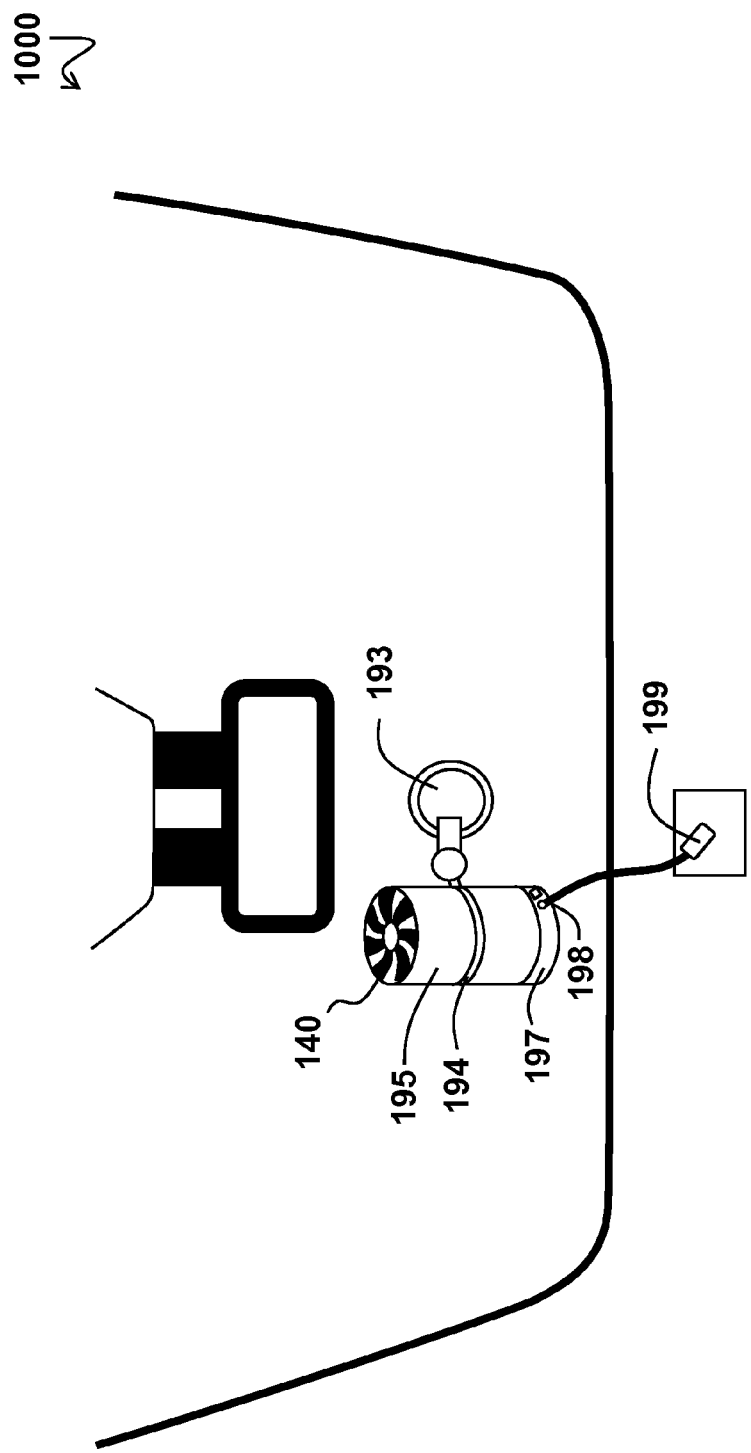
FIG. 10 depicts an exemplary scent dispenser system for use in a vehicle.

FIG. 10 depicts an exemplary scent dispenser system 1000 for use in a vehicle. In an exemplary embodiment, the system 1000 may be attached to a vehicle windshield via a suction mount 193. In some embodiments, the system 1000 may be attached by various means including a cupholder mount and vent mount (not shown). In some embodiments, the system 1000 may work in conjunction with the vents already present in the vehicle to disperse the scents of the flowers more efficiently. The suction mount 193 may be connected to an attachment 194 which encircles the bowl assembly 195 of the system 1000. The bowl assembly 195 may be transparent, opaque, or partially opaque. The system 1000 may contain one or more flowers in a tray (not shown). The scent of the flowers is dispersed by a fan 140 mounted on the top of the system. The base assembly 197 of the system 1000 may comprise a power input 198, which may derive power from an AC adapter 199. In some embodiments, power may be provided by batteries, solar panels facing a window in the vehicle, and/or one or more of the above-mentioned power sources working in tandem depending on the power availability, e.g., activating a battery source if cloud cover inhibits power from an attached solar panel.

One of ordinary skill in the art will appreciate that the elements, components, steps, and functions described herein may be further subdivided, combined, and/or varied, and yet, still remain within the spirit of the embodiments of the invention. Accordingly, it should be understood that various features and aspects of the disclosed embodiments may be combined with, or substituted for one another in order to form varying modes of the invention, as disclosed by example. It is intended that the scope of the present invention herein disclosed by examples should not be limited by the particular disclosed embodiments described above. Accordingly, the invention has been disclosed by way of example and not limitation, and reference should be made to the following claims to determine the scope of the present invention.

What is claimed is:

1. A device comprising:
   a base assembly comprising one or more alignment grooves;
   a controller disposed within the base assembly;
   a bowl assembly comprising one or more alignment grooves, wherein the bowl assembly is configured to detachably attach to the base assembly, and wherein the one or more alignment grooves of the base assembly are configured to align with the one or more alignment grooves of the bowl assembly;
   at least one screen disposed within the bowl assembly in a position parallel to a bottom surface of the bowl assembly, wherein the at least one screen comprises a plurality of apertures configured to hold one or more flowers;
   at least one row of air inlets on the surface of the bowl assembly at a vertical position above the at least one screen and proximate to a position of the space configured to hold one or more flowers;
   a top assembly configured to detachably attach to the bowl assembly, wherein the top element comprises at least one vent; and
   a fan disposed within the top assembly, wherein the fan is electrically connected to the controller within the base assembly by a detachably attachable electrical conduit in the bowl assembly; and
   wherein the controller is configured to execute at least one of: turn the fan on responsive to a user input, cycle the fan between on and off modes at a regular set interval of time responsive to a user input, and turn the fan off responsive to a user input.

2. The device of claim 1 wherein the device further comprises one or more lights and wherein the one or more lights are configured, by the controller, to turn on during at least one of: when the fan is on, and when the fan is cycling between on and off modes.

3. The device of claim 1 wherein the device further comprises one or more speakers and wherein the one or more speakers are configured, by the controller, to turn on during at least one of: when the fan is on, and when the fan is cycling between on and off modes.

4. The device of claim 1 wherein the user input is at least one of: a two-way switch, a three-way switch, and a prompt from a remote device.

5. The device of claim 4 wherein the remote device is configured to execute at least one of: a web application and a smartphone application.

6. The device of claim 1 wherein the bowl assembly further comprises a screen support, wherein the screen support is configured to detachably attach to the screen.

7. The device of claim 6 wherein the screen support is configured to detachably attach to the screen by at least one of: a screw, a press fit, and one or more magnets.

8. The device of claim 6 wherein the device further comprises a second screen comprising a plurality of apertures, and wherein the second screen detachably attaches to the screen support.

9. The device of claim 8 wherein the second screen is vertically separated from the first screen by a distance, and wherein the plurality of apertures of the second screen vertically align with the plurality of apertures of the screen.

10. The device of claim 1 wherein the fan further comprises a fan mounting ring, and wherein the fan mounting ring is detachably attached to the top assembly.

11. The device of claim 1 further comprising a second fan and a second screen.

12. The device of claim 11 further comprising a third fan and a third screen.

13. The device of claim 1 further comprising a suction cup mount.

14. The device of claim 1 wherein the at least one vent is movable to direct air from the fan in a first direction.

15. The device of claim 14 wherein the at least one vent is movable to direct air from the fan in the first direction and a second direction.

16. The device of claim 1 wherein a bottom portion of the bowl assembly vertically below the at least one screen is configured to hold a liquid.

17. The device of claim 16 wherein the bowl assembly further comprises an indent configured to guide any liquid being emptied from the bowl assembly.

18. The device of claim 17 wherein the indent further comprises the electrical conduit.

19. A device comprising:
- a base element, wherein the base element comprises a controller;
- a center element disposed atop the base element, wherein the center element comprises a transparent material;
- at least one tray disposed within the center element, wherein the at least one tray is configured to hold a plant having a scent in an upright position; and
- a top element disposed atop the center element, wherein the top element comprises at least one fan and at least one vent; and
- wherein the device is configured to operate the at least one fan of the top element from the controller of the base element to draw air over the at least one tray of the center element and to disperse this air out of the at least one vent of the top element, wherein the dispersed air comprises the scent of a plant held in the at least one tray.

20. The device of claim 19 wherein the controller is further configured to operate the fan in at least one of three modes: an on mode configured to keep the fan on constantly, a cycle mode configured to cycle the fan at regular intervals, and an off mode configured to turn off the fan.

* * * * *